(12) United States Patent
Maître (10) Patent No.: US 7,448,870 B2
(45) Date of Patent: Nov. 11, 2008

(54) HANDPIECE FOR DENTAL OR SURGICAL USE WITH LOCKING MECHANISM

(75) Inventor: Luc Maître, Epauvillers (CH)

(73) Assignee: Bien-Air Holding S.A., Bienne (CH)

( * ) Notice: Subject to any disclaimer, the term of this patent is extended or adjusted under 35 U.S.C. 154(b) by 396 days.

(21) Appl. No.: 10/558,674

(22) PCT Filed: Feb. 17, 2005

(86) PCT No.: PCT/EP2005/001612

§ 371 (c)(1),
(2), (4) Date: Nov. 30, 2005

(87) PCT Pub. No.: WO2005/089666

PCT Pub. Date: Sep. 29, 2005

(65) Prior Publication Data

US 2007/0054239 A1   Mar. 8, 2007

(30) Foreign Application Priority Data

Feb. 17, 2004   (EP) ................................. 04003520

(51) Int. Cl.
*A61C 1/10* (2006.01)
(52) U.S. Cl. ...................................................... 433/114
(58) Field of Classification Search ......... 433/114–131; 279/30, 74, 75, 76, 82, 905; 606/80, 79, 606/167, 170; 81/177.2, 177.85; 7/167
See application file for complete search history.

(56) References Cited

U.S. PATENT DOCUMENTS

| | | | |
|---|---|---|---|
| 3,488,850 A | 1/1970 | Lieb et al. | |
| 3,631,597 A | 1/1972 | Lieb et al. | |
| 3,902,248 A | 9/1975 | Bareth | |
| 4,260,381 A | 4/1981 | Eibofner et al. | |
| 6,126,442 A | 10/2000 | Knorpp et al. | |
| 2002/0151902 A1 | 10/2002 | Riedel et al. | |
| 2003/0023256 A1* | 1/2003 | Estes et al. ................... | 606/167 |

OTHER PUBLICATIONS

Office Action issued in corresponding U.S. Appl. No. 11/045,098,dated Mar. 27, 2008.

* cited by examiner

*Primary Examiner*—Melba Bumgarner
*Assistant Examiner*—Sunil K Singh
(74) *Attorney, Agent, or Firm*—Griffin & Szipl, P.C.

(57) ABSTRACT

The handpiece includes at the front a collet arranged for strongly gripping the shank of a removable tool housed in guide bores. The collet includes two or several arms attached to an annular part of the collet to grip the tool shank. Preferably, the collet arms are levers each having a support surface which is far from the jaw and on which a gripping mechanism exerts a force which is multiplied by the lever. The gripping mechanism includes a sliding sleeve having an inner conical surface which produces the force on the collet levers via balls. This arrangement enables a smaller gripping spring to be used, or such spring to be omitted. The balls of the releasing mechanism are guided in helical slots having a flexible lateral strip which holds the gripping mechanism in position via a snap fit.

10 Claims, 6 Drawing Sheets

Fig. 9

# HANDPIECE FOR DENTAL OR SURGICAL USE WITH LOCKING MECHANISM

This application claims priority on PCT/EP2005/001612 of Feb. 17, 2005, which claims priority from European Patent Application No. 04003520.6, filed Feb. 17, 2004.

BACKGROUND OF THE INVENTION

The present invention concerns a handpiece for dental or surgical use, of the type comprising: a hollow shaft rotating about a longitudinal axis and mounted via roller bearings in a fixed tubular shaft; a collet mounted in a front end of the hollow shaft and having a central channel for receiving the shank of a removable tool, the collet including axial arms distributed around the axis and each provided with a clamping or gripping jaw in the central channel; a gripping mechanism carried by the hollow shaft and arranged to exert a centripetal force on a support surface for each arm of the collet to grip the shank of the tool between the jaws of the collet; and a releasing mechanism carried at least in part by the fixed shaft and arranged to act on the gripping mechanism at least so as to release the collet.

In usual handpieces, like those disclosed in FR Patent Application No. 2 191 869 corresponding to U.S. Pat. No. 3,902,248, the jaws are located at one end of the collet which has external support surfaces of conical shape, which engage in an inner cone of a tubular part which thus grips the end of the collet on the shank of the tool. For example, the collet is slidably mounted in the hollow shaft, it jaws and its external support surfaces are at its front end for cooperating with the front orifice of the shaft, and a collet spring keeps the collet gripped by pulling it axially backwards. The releasing mechanism comprises an outer sleeve which is connected to the body of the instrument by a screw system and which acts as a control member. When the user pivots the sleeve, the latter moves forward driving an inner bush which compresses the collet spring and moves the collet forward to release it from the cone that was gripping it.

In cases where the tool carried by the handpiece has to support relatively high stress, particularly as far as torque and axial force is concerned, the collet has to grip quite hard. This means the collet spring has to have quite high axial force, and high friction forces on the conical surfaces which transform the axial force into radial clamping or gripping forces. The releasing mechanism has to be able to overcome these forces by applying sufficient axial thrust to the sliding member biased by the collet spring. This axial thrust is then transmitted to the frame of the handpiece via at least one of the roller bearings supporting the rotating shaft. Most of the time, like in the construction according to FR 2 191 869, this thrust is exerted forwards and thus loads the roller bearings in the opposite direction to the axial loads that the tool will undergo in use, i.e. the roller bearings have to be designed to withstand axial loads in both directions.

Moreover, a relatively strong collet spring has a relatively large mass, which constitutes a considerable drawback for a part that rotates very fast and which cannot generally be centred with precision. The resulting vibrations increase with the mass of the spring.

In the handpiece disclosed in U.S. Pat. No. 3,631,697, the collet and its collet spring device are of the same type as that described hereinbefore, with the same drawbacks. In order to overcome the force of the collet spring, a releasing mechanism is provided comprising balls engaged both in helical slots of a fixed tube and in longitudinal grooves of a pivoting sleeve that acts as a manual control.

A handpiece without any collet spring is disclosed in U.S. Pat. No. 3,488,850. The collet has conical external surfaces cooperating with annular parts which produce its gripping and it is mounted in the hollow shaft with longitudinal play. The front end of the collet is not supported by the shaft, but by a front bearing fixed in an axially mobile nose to act as manual control member. In order to do this, the nose is mounted via a threading onto the body of the handpiece, such that the operator can rotate it to move the front bearing backwards or forwards in order to tighten or release the collet. A big drawback of this system is that it imposes a strong axial load on the bearings while the collet is being clamped, and thus during work. Moreover, the front bearing support system is not rigid enough to prevent the tool vibrating as soon as speed is high.

SUMMARY OF THE INVENTION

It is an object of the present invention to prevent the aforementioned drawbacks of the prior art, owing to an arrangement with strong gripping at the collet jaws, while limiting the axial forces occurring in the gripping and releasing mechanism. In particular, the gripping and releasing mechanisms should be arranged so as to facilitate manoeuvring of the collet and prevent inadvertent manipulations. It is an additional object of the invention to simplify the arrangement of the roller bearings of the main bearings of the handpiece, in particular by reducing the axial loads on at least one of them.

According to a first aspect of the invention, there is provided a handpiece of the type indicated in the preamble hereinbefore, characterized in that the gripping mechanism comprises a sliding sleeve mounted on the hollow shaft and, for each arm of the collet, a transmission element arranged in a radial hole of the hollow shaft between said arm support surface and an inner cam surface of the sliding sleeve, and in that the releasing mechanism comprises a sliding collar arranged in the fixed tubular shaft and provided with an external annular groove, a rotating bush arranged around the fixed tubular shaft, connected to a manual control member and provided with inner axial grooves, and a set of balls each engaged in one of said axial grooves, in a helical slot of the fixed tubular shaft and in said annular groove, such that rotation of the rotating bush in a determined direction moves the sliding collar axially to drive the sliding sleeve of the gripping mechanism so as to release the collet.

With this combination of features, quite strong gripping can be obtained for the collet without large axial forces appearing in the rotating part of the handpiece, and the gripping and releasing devices can also be lightened owing to this reduction in stress. According to a preferred embodiment, the helical slot of the releasing mechanism can thus include, laterally, close to the end thereof where the ball is situated when the releasing mechanism is in the inactive position, a flexible tongue which holds by snap fitting ball into this position, in order to prevent inadvertent releasing.

The sliding sleeve can be drawn in the gripping direction by a relatively small spring. In a particularly advantageous variant, a hollow can be arranged in the cam surface, forming a catch that holds the sliding sleeve in place via the resilience of the collet arms, which allows the usual clamping spring to be omitted. Consequently, the releasing manoeuvre no longer has to overcome the axial thrust caused by the spring.

According to a second aspect, the invention concerns a handpiece of the type indicated in the preamble hereinbefore, characterized in that the gripping mechanism includes a sliding sleeve mounted on the hollow shaft and, for each arm of the collet, a transmission element arranged in a radial hole of the hollow shaft between said arm support surface and an inner cam surface of the sliding sleeve, and in that the gripping mechanism includes a sliding collar arranged in the fixed tubular shaft and activated by a manual control member such that the latter can move the sliding collar axially to drive the sliding sleeve of the gripping mechanism so as to release the collet, in that said cam surface includes a first hollow, provided with an axially inclined surface, and a second hollow, shallower than the first and separated therefrom by a projecting portion, and in that the arms of the collet are resilient, such that the second hollows form a catch that holds the sliding sleeve in place when said transmission elements are engaged in the second hollows by the resilience of the collet arms. This also provides the advantages mentioned in the preceding paragraph.

According to a preferred embodiment, each arm of the collet is formed by a lever, a first end of which is attached to the annular part by a hinge and whose said support surface is axially at a distance from said hinge, the jaw being located closer to the hinge than to the support surface. Consequently said centripetal forces that have to be exerted by the gripping mechanism can be reduced, since they are multiplied by the collet levers to exert a strong gripping force on the tool.

Other features and advantages of the present invention will appear more clearly in the following description of various embodiments, given by way of non-limiting examples with reference to the annexed drawings.

BRIEF DESCRIPTION OF THE DRAWINGS

FIG. 9 is a detailed longitudinal cross-sectional view showing a second embodiment, owing to an alteration to the ball gripping mechanism visible in FIG. 2a.

DETAILED DESCRIPTION OF EMBODIMENTS OF THE INVENTION

Figure 1:
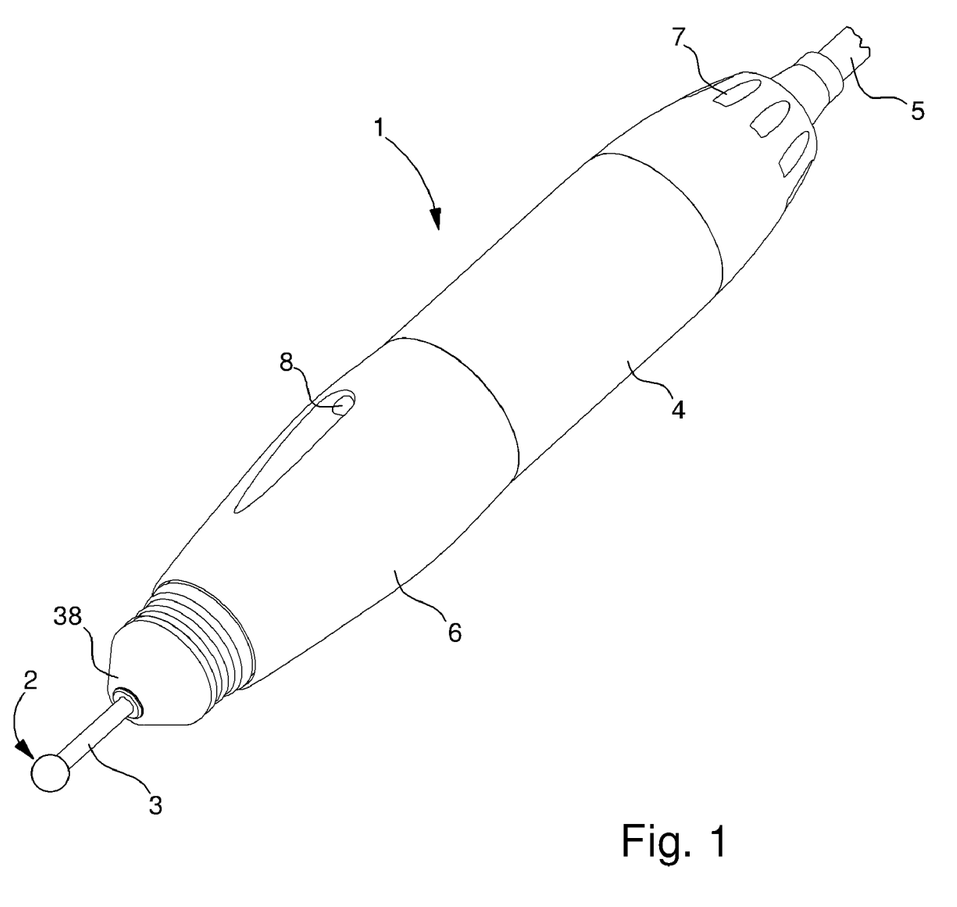
FIG. 1 is a schematic perspective view of a handpiece according to the invention.

FIG. 1 shows a handpiece 1 for dental or surgical use, wherein the various embodiments of the invention, which will be described hereinafter, can be found. The handpiece is fitted with a removable rotating tool 2 having a cylindrical shank 3 which is clamped or gripped into a rotating collet of handpiece 1. The latter contains a motor, in this case an electric motor, for rotating tool 2 at high speed. The motor is housed in the main body 4 of the handpiece and it is powered and controlled from an external unit via an electric cable 5 connected to the back of the handpiece. The operator controls the gripping and releasing of the collet by rotating a sleeve 6, rotatably mounted on body 4, in one direction or the other. References 7 and 8 design ventilation vents. This type of instrument finds application particularly in dental surgeries, in dental laboratories and in micro-surgical techniques. In the examples shown here, it is an instrument for a dental laboratory, using tools whose shank has a standardised diameter of 2.35 mm.

With reference to FIGS. 2 to 5, a first embodiment of collet 10 for gripping the tool and the gripping and releasing mechanisms for the collet will now be described. Collet 10 is located in the front end of the handpiece, inside a hollow rotating shaft 11 coupled to shaft 12 of electric motor 13. Shaft 11 is supported by ball bearings 14 and 15 in a tubular shaft 16 fixed to body 4 of the handpiece and it can thus rotate at speeds of the order of 50, 000 rounds per minute in the instrument shown here. However, a collet such as collet 10 can also be used in instruments whose tool can rotate at several hundred thousand rounds per minute, particularly with air turbine drive.

Figure 2A:
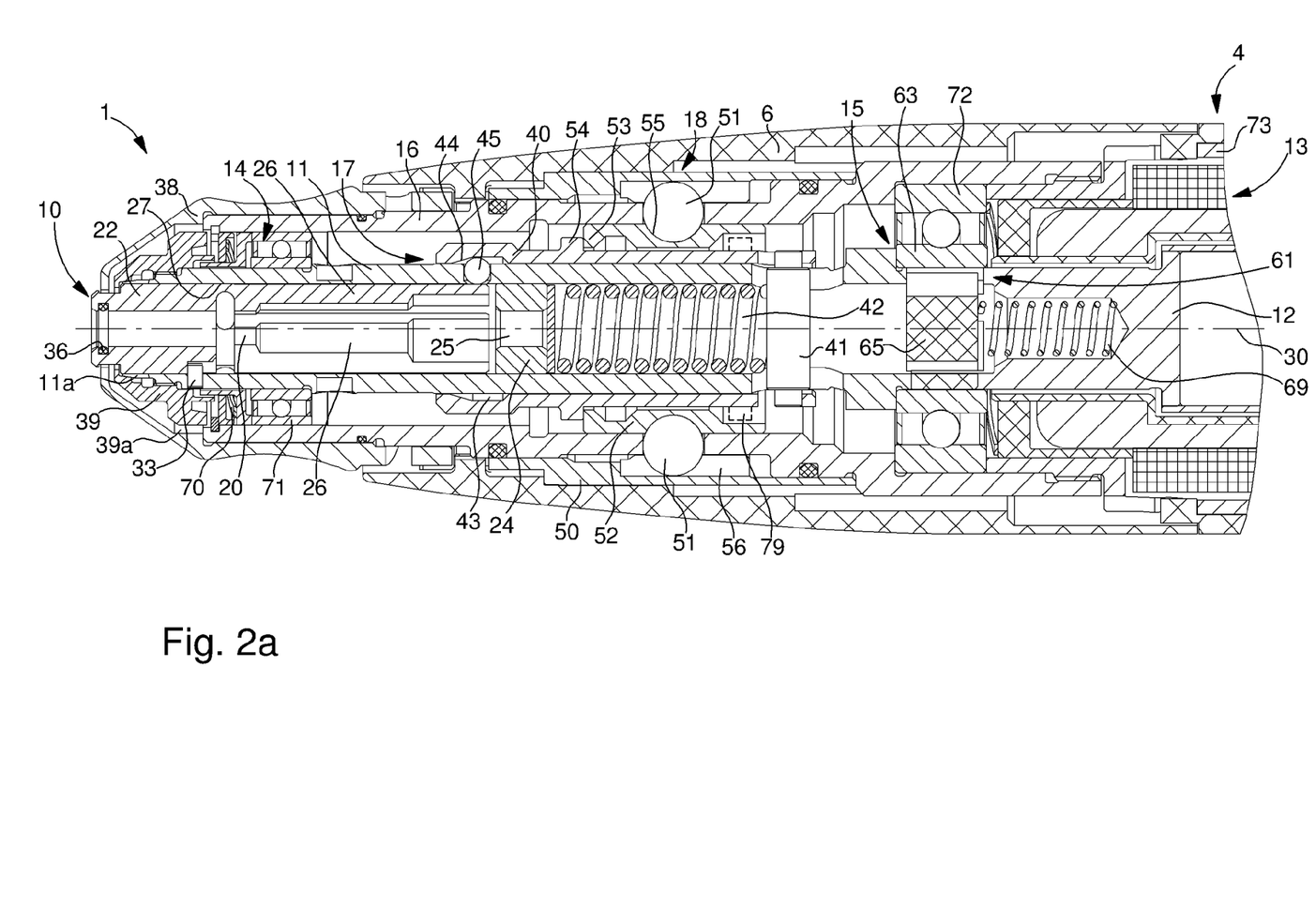
FIG. 2, divided into two parts 2a and 2b, is a longitudinal cross-section of a first embodiment of the handpiece of FIG. 1, including a collet associated with a ball gripping mechanism.

A mechanism 17 for gripping collet 10 is mounted on shaft 11 and rotates with the latter. A mechanism 18 for releasing the collet, controlled by rotating sleeve 6, is mounted on non-rotating shaft 16 and can act on gripping mechanism 17 in order to release the tool when the rotation has stopped. These mechanisms will be described in detail hereinafter.

Figure 3:
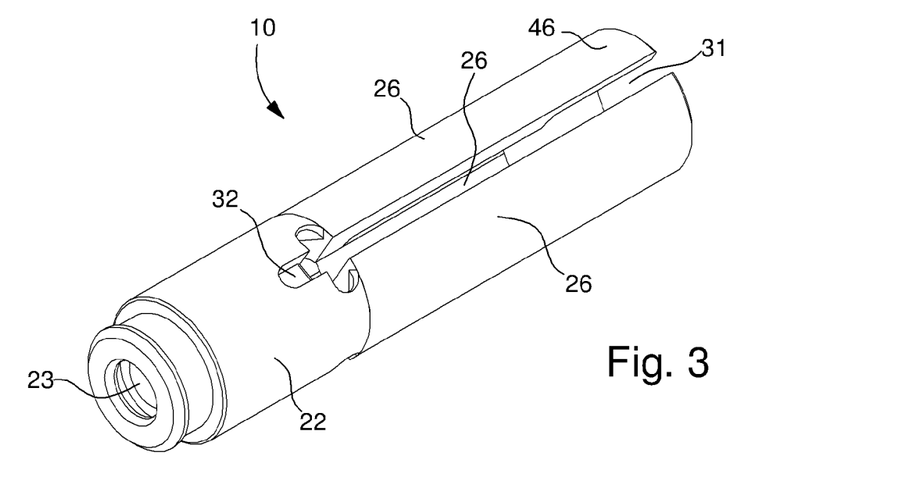
FIGS. 3 to 5 show the collet visible in FIG. 2, respectively in perspective, longitudinal cross-section and side view.
Figure 4:
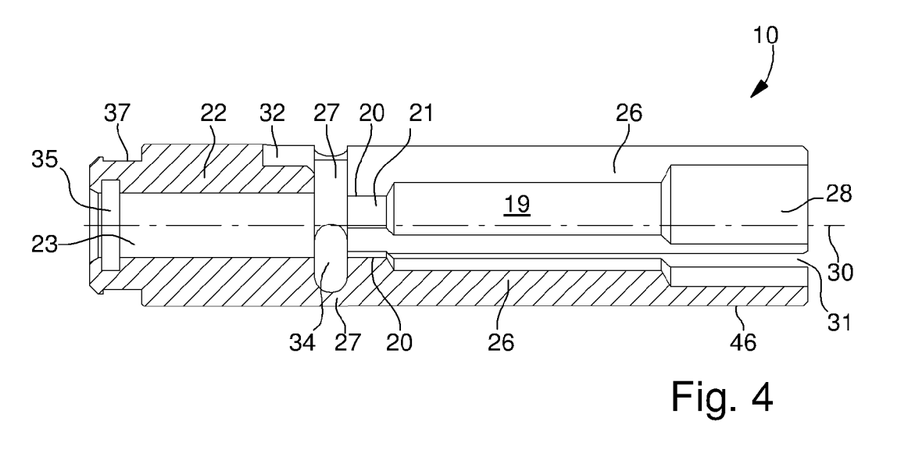
Figure 5:
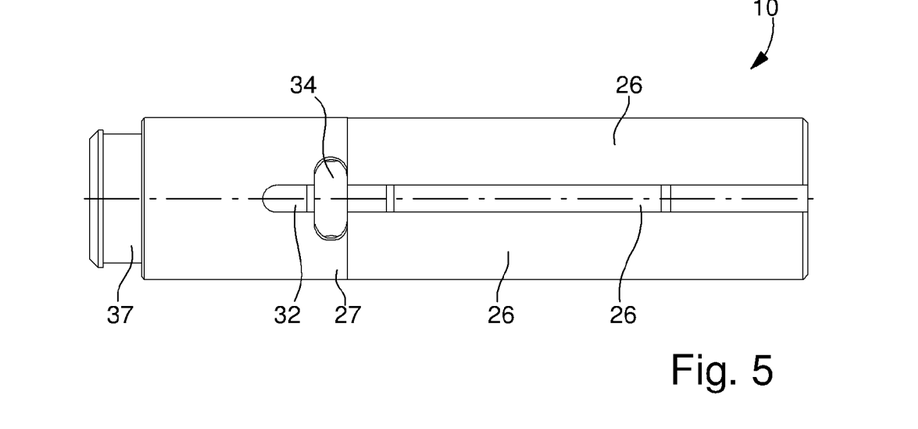

FIGS. 3 to 5 show more particularly the first embodiment of collet 10, which comprises here three jaws 20 regularly distributed around a central channel 19 of the collet, receiving shank 3 of the tool. Each jaw 20 has a portion of cylindrical surface 21 for applying against the shank of the tool.

At the front, collet 10 includes a substantially cylindrical entry barrel 22, provided with an axial bore 23 calibrated with a high level of precision in order to centre the tool as perfectly as possible. It will be noted in FIG. 2 that a back guide barrel 24 is secured in shaft 11 behind collet 10 and comprises a central bore 25 for guiding the end of the shank of the tool.

Each jaw 20 forms an integral part of a respective lever 26, which extends axially backwards from entry barrel 22, to which it is attached by a flexible part 27 forming a kind of hinge on which lever 26 can pivot in the direction of the rotational axis 30 of the shaft. On each lever 16, jaw 20 is much closer to flexible part 27 than to the free end 28 of the lever, such that any radial force applied to the lever close to its end 28 produces a very high gripping force on jaw 20.

Collet 10 shown in the drawings is preferably made in a single metal part, for example, steel. Levers 26 are separated from each other by radial slots 31 each extending via a recess 32 into the back of barrel 22. A pin 33, which secures collet 10 and hollow shaft 11 in rotation, is engaged in each recess 32. Transverse slots 34 reduce the thickness of levers 26 at their base and thus define the flexible parts 27 in three peripheral regions of the transverse section of the collet. At the front of entry barrel 22, there is provided an inner annular groove 35 for an O-ring joint 36 and an external annular groove 37 for the lips of a fixed cap 38 and a nut 39 screwed onto shaft 11 to hold collet 10 axially. Nut 39 is provided with ventilation wings 39a for creating light air pressure under cap 38 to prevent dirt entering through the slot between the cap and barrel 22. Further, nut 39 grips end 11 a of hollow shaft 11 radially against barrel 22, this end being thinned and divided into flexible strips by axial slots. This centres collet 10 in the hollow shaft without any play.

In a variant that is not shown here, entry barrel 22 can be a distinct part that does not form part of collet 10. The front of the latter is then formed of a short annular portion to which levers 26 are attached by a hinge. This annular part can be a distinct part of the levers, depending upon requirements, but an embodiment in one piece is generally preferable.

Gripping mechanism 17 includes a sleeve 40 which is mounted so as to slide about hollow shaft 11, to which it is secured in rotation by a transverse bar 41 engaged in longitudinal slots of shaft 11 and sleeve 40. A compression spring 42, abutting via a washer on back guide barrel 24, pushes bar 41 axially backwards. The front end of sleeve 40 includes an inner groove 43 delimited at the front by a conical surface 44. Three balls 45 are housed in corresponding holes 78 (see FIG. 9) of hollow shaft 11 and have a diameter that corresponds to the distance between the inner surface of shaft 11 and the bottom of groove 43 of sleeve 40. Each ball 45 abuts on the external surface of one of levers 26 of collet 10, close to end 28 of the lever.

When sleeve 40 is released from releasing mechanism 18, it tends to slide backwards via the effect of the axial thrust of spring 42, such that its conical surface 44 pushes the end of each lever 26 inwards radially via the corresponding ball 45. By pivoting the lever on flexible part 27, this force is transmitted in a multiplied manner onto jaw 20 of the lever and thus grips the shank of the tool very tightly, and this permanently during work. Those skilled in the art will understand that with such a gripping mechanism, levers 26 of the collet can be either rigid, or slightly flexible. If they are rigid, the radial movements of their ends are simply a little smaller, and the same is true for the axial movement of sleeve 40. In both cases, a high gripping force is permanently maintained on jaws 20 even if the force of spring 42 is relatively modest, owing to the lever effect of the collet and also owing to the small inclination of conical surface 44 relative to axis 30. Another effect of this slight inclination is that the centrifugal force acting on levers 26 cannot overcome the effect of spring 42. It should also be noted that the transmission of force via balls 45 occurs with very little friction, which also contributes to maintain a determined gripping force. However, these balls are not indispensable, since they could be replaced by other transmission elements passing through shaft 11 and capable of pushing levers 26 inwards.

Figure 6:
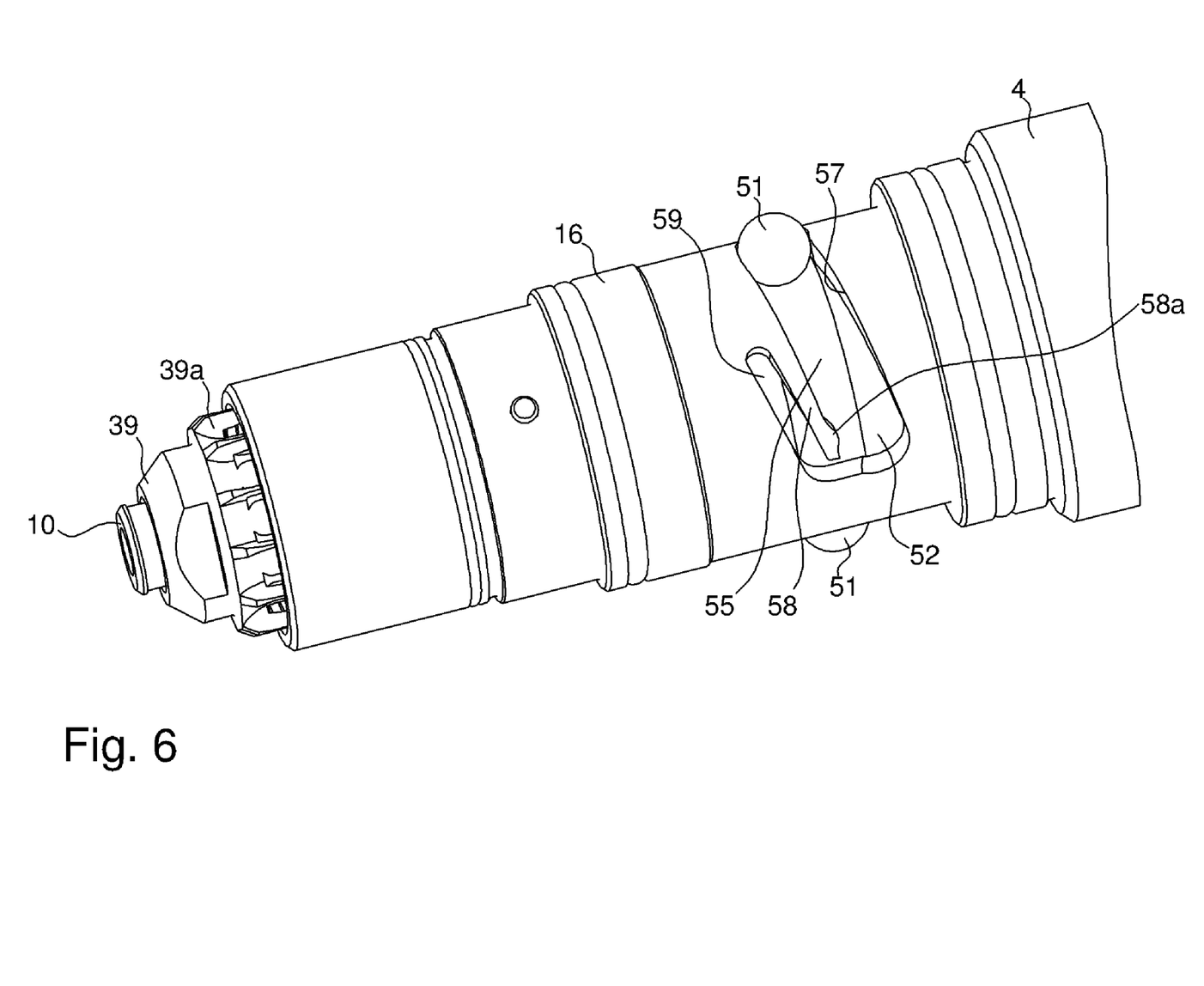
FIG. 6 is a partial perspective view of a collet gripping and releasing control device.

Releasing mechanism 18 is designed to push sleeve 40 forwards, against the force of spring 42, when the user rotates control sleeve 6 on body 4 in the corresponding direction. It includes a bush 50 connected in rotation to control sleeve 6, one or several balls 51, in this case two balls symmetrically arranged in relation to axis 30 of the handpiece, and a pusher collar 52 slidably mounted in shaft 16 and having at the front an inner edge 53 for axially abutting against an external thrust collar 54 of sleeve 40 when the latter is not rotating. Balls 51 are engaged in an external annular groove 55 of collar 52. Further, each ball 51 is engaged in a corresponding axial groove 56 of bush 50 and in an inclined slot 57 (FIG. 6) of tubular shaft 16. The outline of each slot 57 is substantially helical, to determine a certain axial movement of ball 51, and the ends thereof can be slightly bent in order to better define a stop position for the ball. In the preferred embodiment shown in FIG. 6, the back end of each slot 57, corresponding to the withdrawn position of collar 52 and thus to a state in which collet 10 is tightened, is fitted with a flexible strip 58 the end of which has a raised portion 58a which reduces the width of slot 57 locally, in order to spring fit ball 51 at the end of slot 57. This has the effect of holding rotating control sleeve 6 resiliently in order to prevent any inadvertent activation and to allow the user to feel that it is going to leave the normal collet working position. It should be noted that flexible strip 58 is made simply by machining an additional slot 59 in tubular shaft 16. This slot is substantially parallel to slot 57, to which it is connected around the end of strip 58.

Figure 7:
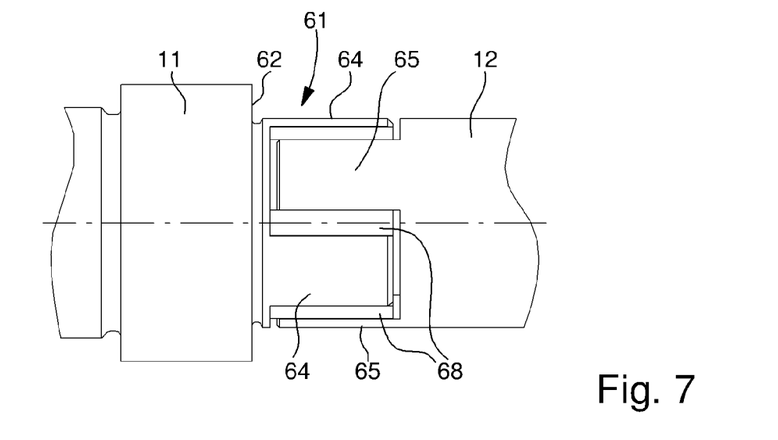
FIG. 7 is a view of the coupling between the two shafts of the handpiece.
Figure 8:
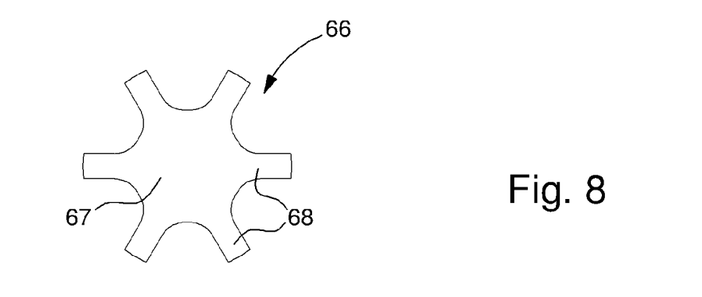
FIG. 8 represents an insert of the coupling

One remarkable aspect of the handpiece, illustrated particularly in FIG. 2, is the fact that the rotating part is supported by only three bearings, namely front ball bearing 14, central ball bearing 15 and a back ball bearing 60, the two coaxial shafts 11 and 12 both being supported by central ball bearing 15 inside which they are connected to each other in rotation by a positive coupling 61 shown more particularly in FIGS. 2, 7 and 8. The back end of hollow shaft 11 has a shoulder 62 which abuts against inner collar 63 of ball bearing 15. It also has a group of jaw clutches 64 which is driven into collar 63, in this case three jaw clutches distributed at 120 degrees from each other over the circumference. The front end of shaft 12 of the motor is inserted into inner collar 63 of ball bearing 15, preferably so as to be able to make small axial movements therein that can arise from thermal expansion, axial play of the bearings and other tolerances. This end of shaft 12 also includes jaw clutches 65 extending axially between jaw clutches 64 of the other shaft, to ensure the transmission of torque in both directions between the two shafts. An insert 66, preferably made of synthetic material, includes a central cylindrical body 67 and radial wings 68, which are inserted between adjacent jaw clutches 64 and 65 to act as bearings. Moreover, insert 66 is pre-stressed axially against hollow shaft 11 by a compression spring 69 housed in shaft 12 and whose role will appear hereinafter.

Figure 2B:
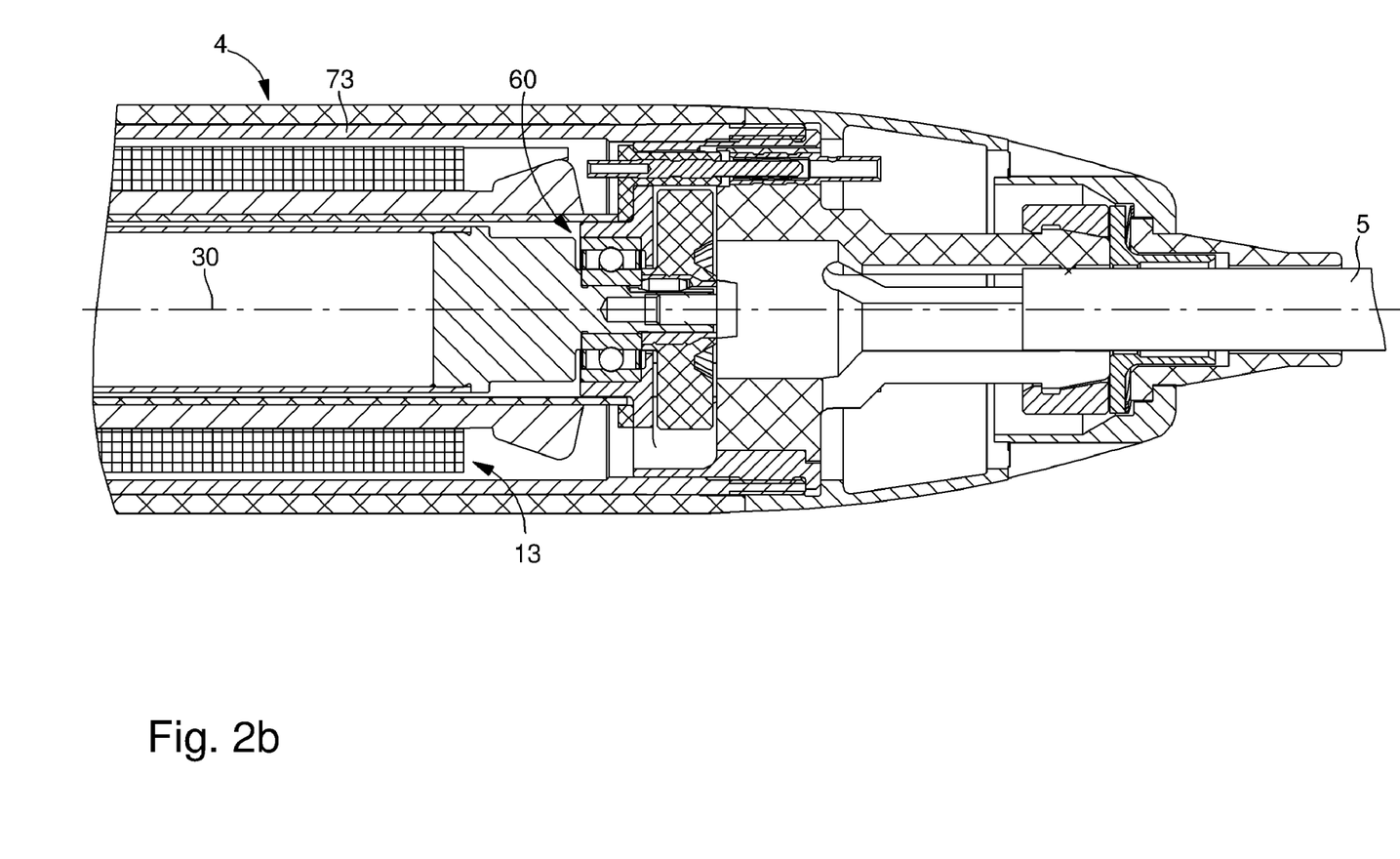

Front bearing 14 is pre-stressed by means of a diaphragm spring 70 which pushes outer collar 71 of the bearing, able to slide into tubular shaft 16, backwards. This axial pre-stress is transmitted through bearing 14 and shaft 11 to the area of central bearing 15, where it is distributed over insert 66 and shaft 12 of the motor, in equal measure to the axial thrust of spring 69, and the remainder into central bearing 15 in the form of a pre-stress which returns to tubular shaft 16 via external collar 72 of the bearing. The axial force that spring 69 exerts on shaft 12 obviously constitutes the axial pre-stress of back bearing 60. Because of the axial play of coupling 61 between the two shafts, this load does not vary when the user exerts an axial thrust on the tool, since this thrust is entirely absorbed by central roller bearing 15 whose external ring 72 abuts against the end of a tubular element 73 of body 4, screwed into the back end of shaft 16.

The construction described hereinbefore offers the same advantages as a conventional construction with four bearings from the point of view of the absorption of axial loads, but it is considerably shorter and thus allows the total length of the handpiece to be substantially reduced. This reduction in length has the great advantage of increasing the operator's manipulating precision, particularly by reducing the effect of the stress that cable 5 exerts on the back end of the instrument.

Another considerable advantage is that, since the adjacent ends of the two shafts 11 and 12 are supported and centred by the same collar 62, their concentricity is assured without any additional measures.

Figure 9:
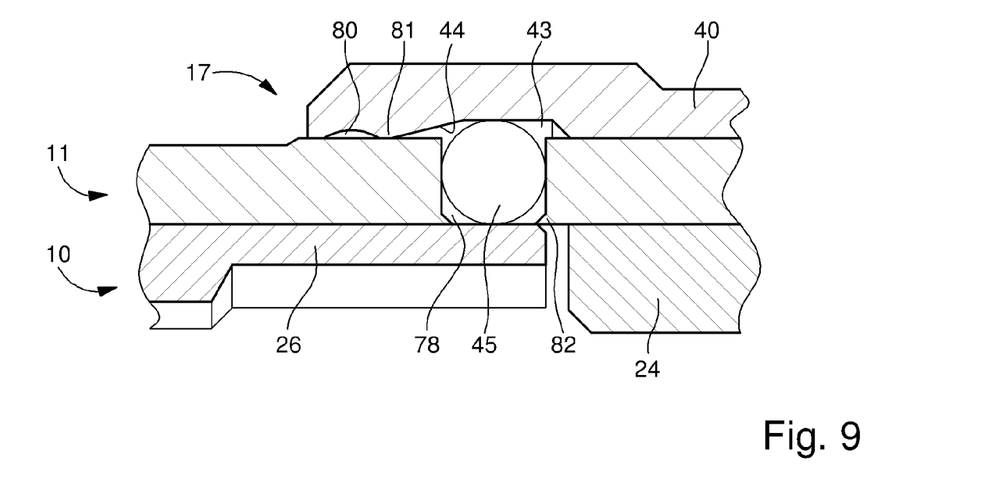

FIG. 9 shows a second embodiment of the gripping mechanism 17, which allows considerable simplification with respect to the first embodiment of the handpiece. Mechanism 17 differs from that described hereinbefore mainly in the arrangement shown in FIG. 9 and the removal of central spring 42 shown in FIG. 2a. Releasing mechanism 18 then acts as gripping and releasing control means. So that it can be snap fitted in the releasing position as well as in the gripping position, slot 55 shown in FIG. 6 can be fitted with a flexible strip 58 at each of its ends.

In FIG. 9, it can be seen that the front end of sleeve 40 is altered simply by adding an annular groove 80 with a profile in the arc of a circle, said groove being separated from conical surface 44 by a short portion of cylindrical surface which forms a radial projection 81 in relation to the neighbouring surfaces. In this case, each lever 26 of collet 10 is preferably slightly flexible, which allows gripping mechanism 17 to operate in the following manner.

FIG. 9 shows the releasing position, in which each ball 45 can go as far as the bottom of groove 43, such that each lever 26 of collet 10 can move away until it is applied against the inner surface of hollow shaft 11. Jaws 20 of collet 10 are then spaced at a maximum distance and shank 3 of the tool can be inserted or removed.

In order then to tighten collet 10, sleeve 40 is drawn back by rotating control sleeve 6 as in the preceding example, but the axial movement of sleeve 40 is larger, since it occurs until groove 80 is placed on balls 45. In order for sleeve 40 to be driven backwards by collar 52 visible in FIG. 2a, a removable stop collar 79 (shown in dotted lines in the drawing) can be fixed around its back end. First of all, the passage of conical surface 44 over balls 45 pushes levers 26 towards the centre and makes them bend when the jaws of the collet meet sufficient resistance on the tool shank. Owing to this bending, cylindrical projection 81 can pass over the balls, then groove 80 will snap onto the balls and hold sliding sleeve 40 in place solely due to the support force of levers 26 on balls 45.

Releasing is carried out in substantially the same way as in the first embodiment, by rotating control sleeve 6 (FIG. 2a) which causes collar 53 and the sleeve to move forward to the position shown in FIG. 9.

The possibility of omitting central spring 42 shown in FIG. 2 offers quite significant advantages. On the one hand, the rotating part is better balanced, since a spring of this type can never be perfectly centred in the bore containing it. The weight gain also contributes to this. On the other hand, omission of this spring reduces the axial forces that releasing mechanism 18 exerts forwards on sliding sleeve 40 and, consequently, on hollow shaft 11. These forces have then to pass into the bearings supporting the shaft, in particular into front bearing 14 which is as small as possible and should not be subjected to too high an axial force. With the arrangement according to FIG. 9, the maximum axial force imparted to shaft 11 during releasing is the force necessary to make balls 45 leave groove 80. The value of this force can easily be pre-determined by the profile given to the groove.

In FIG. 9, a skirt 82, or series of equivalent beaks, is provided on the inner edge of cylindrical hole 78 containing ball 45, in order to hold the latter when collet 10 is removed. Since this skirt is not easy to make, it can be replaced by back barrel 24 slightly encroaching on the opening of hole 78, slightly shortening collet arms 26.

It will be noted that the gripping mechanism 17 described hereinbefore, whether in the embodiment of FIG. 2a or that of FIG. 9, acts only on the peripheral surfaces of collet 10 and not on the end thereof. This makes various lever-effect collet configuration variants possible in accordance with the principles stated here.

If one considers FIG. 2a, one of these variants consists in drawing back (towards the right of the drawing) front guide barrel 24 and incorporating it in collet 10, the two ends of levers 26 then being respectively attached to front barrel 22 and to back barrel 24, the levers also being thin enough to bend radially between the barrels via the action of balls 45. These latter act on support surfaces located substantially midway along the length of the levers. Jaws 20 could then be located both close to front barrel 22 and close to back barrel 24, thus guaranteeing that the tool shank is held without any play at two axially distant points.

Another variant, along the same lines, could consist in arranging two collets like collet 10 head-to-shank and spaced such that they can be placed between the levers of the other collet without touching them inside shaft 11. The jaws of one of the collets would then be at the front while those of the other collet would be further back, thus holding the tool shank without any play at two axially distant points. The gripping mechanism could comprise two sets of balls 45 and possibly two grooves 43 axially shifted in sliding sleeve 40, to act on the respective collets.

Although the examples described hereinbefore only comprise lever collets, it goes without saying that the applications of the invention also extend to hand-held instruments in which the collets or clamping chucks have arms which are not levers, insofar as the gripping mechanism has, above all, to apply a centripetal force to each of said arms.

The invention claimed is:

1. A handpiece for dental or surgical use, including:
a hollow shaft rotating around a longitudinal axis and mounted via bearings in a fixed tubular shaft,
a collet mounted in a front end of the hollow shaft and having a central channel for receiving the shank of a removable tool, the collet including axial arms distributed around the axis and each provided with a jaw in the central channel,
a gripping mechanism carried by the hollow shaft and arranged for exerting a centripetal force on a support surface of each arm of the collet to grip the tool shank between the jaws of the collet, and
a releasing mechanism carried at least in part by a the fixed tubular shaft and arranged for acting on the gripping mechanism at least so as to release the collet,
wherein the gripping mechanism includes a sliding sleeve mounted on the hollow shaft and, for each arm of the collet, a transmission element arranged in a radial hole of the hollow shaft between said support surface of the arm and an inner cam surface of the sliding sleeve, and wherein the releasing mechanism includes a sliding collar arranged in the fixed tubular shaft and actuated by a manual control member such that the latter can move the sliding collar axially to drive the sliding sleeve of the gripping mechanism so as to release the collet, and wherein said cam surface includes a first hollow provided with said inclined surface and also a second hollow that is shallower than the first and separated therefrom by a projecting part and wherein the arms of the collet are resilient, such that the second hollows form a notch which holds the sliding sleeve in place when said transmission elements are engaged in the second hollows by the resilience of the collet arms.

2. The handpiece according to claim 1, wherein the sliding sleeve is not biased by a spring, the releasing mechanism being arranged for moving it axially in both directions, respectively for gripping and releasing the collet.

3. The handpiece according to claim 1, wherein the sliding sleeve is not biased by a spring, the releasing mechanism being arranged for moving it axially in both directions, respectively for gripping and releasing the collet.

4. The handpiece according to claim 1, wherein said transmission elements are balls.

5. The handpiece according to claim 1, wherein each arm of the collet includes a lever, a first end of which is attached to an annular part of the collet by a hinge and whose said support surface is axially distant from said hinge, the jaw being located closer axially to the hinge than to the support surface.

6. The handpiece according to claim 1, wherein each arm of the collet includes a lever, a first end of which is attached to an annular part of the collet by a hinge and whose said support surface is axially distant from said hinge, the jaw being located closer axially to the hinge than to the support surface.

7. The handpiece according to claim 5, wherein the annular part and the levers of the collet are made in a single piece, said hinge of each lever being a resilient hinge and said annular part including a guide barrel for the tool shank.

8. The handpiece according to claim 6, wherein the annular part and the levers of the collet are made in a single piece, said hinge of each lever being a resilient hinge and said annular part including a guide barrel for the tool shank.

9. A handpiece for dental or surgical use, including:
- a hollow shaft rotating about a longitudinal axis and mounted via bearings in a fixed tubular shaft,
- a collet mounted in a front end of the hollow shaft and having a central channel for receiving the shank of a removable tool, the collet including axial arms distributed around the axis and each provided with a jaw in the central channel,
- a gripping mechanism carried by the hollow shaft and arranged for exerting a centripetal force on a support surface of each arm of the collet to grip the tool shank between the jaws of the collet, and
- a releasing mechanism carried at least in part by the fixed tubular shaft and arranged for acting on the gripping mechanism at least so as to release the collet,
- wherein the gripping mechanism includes a sliding sleeve mounted on the hollow shaft and, for each arm of the collet, a transmission element arranged in a radial hole of the hollow shaft between said support surface of the arm and an inner cam surface of the sliding sleeve, and wherein the releasing mechanism includes a sliding collar arranged in the fixed tubular shaft and provided with an external annular groove, a rotating bush arranged around the fixed tubular shaft, connected to a manual control member and provided with inner axial grooves, and a set of balls each engaged in one of said axial grooves, in a helical slot of the fixed tubular shaft and in said annular groove, such that rotating the rotating bush in a determined direction moves the sliding collar axially to drive the sliding sleeve of the gripping mechanism so as to release the collet, said helical slot including on one of its edges, close to the end thereof where the ball is located when the releasing mechanism is in the inactive position, a flexible strip which retains the ball in this position via a snap fit, said flexible strip being formed between said helical slot and an additional slot substantially parallel thereto, said strip having, close to the end thereof, a raised portion which reduces the width of the helical slot locally.

10. A handpiece for dental or surgical use, including:
- a hollow shaft rotating about a longitudinal axis and mounted via bearings in a fixed tubular shaft,
- a collet mounted in a front end of the hollow shaft and having a central channel for receiving the shank of a removable tool, the collet including axial arms distributed around the axis and each provided with a jaw in the central channel,
- a gripping mechanism carried by the hollow shaft and arranged for exerting a centripetal force on a support surface of each arm of the collet to grip the tool shank between the jaws of the collet, and
- a releasing mechanism carried at least in part by a the fixed tubular shaft and arranged for acting on the gripping mechanism at least so as to release the collet,
- wherein the gripping mechanism includes a sliding sleeve mounted on the hollow shaft and, for each arm of the collet, a transmission element arranged in a radial hole of the hollow shaft between said support surface of the arm and an inner cam surface of the sliding sleeve, and wherein the releasing mechanism includes a sliding collar arranged in the fixed tubular shaft and provided with an external annular groove, a rotating bush arranged around the fixed tubular shaft, connected to a manual control member and provided with inner axial grooves, and a set of balls each engaged in one of said axial grooves, in a helical slot of the fixed tubular shaft and in said annular groove, such that rotating the rotating bush in a determined direction moves the sliding collar axially to drive the sliding sleeve of the gripping mechanism so as to release the collet, said cam surface including an axially inclined surface such as a conical surface and a first hollow provided with said inclined surface and also a second hollow that is shallower than the first and separated therefrom by a projecting part, the arms of the collet being resilient, such that the second hollows form a notch which holds the sliding sleeve in place when said transmission elements are engaged in the second hollows by the resilience of the collet arms.

* * * * *